United States Patent [19]

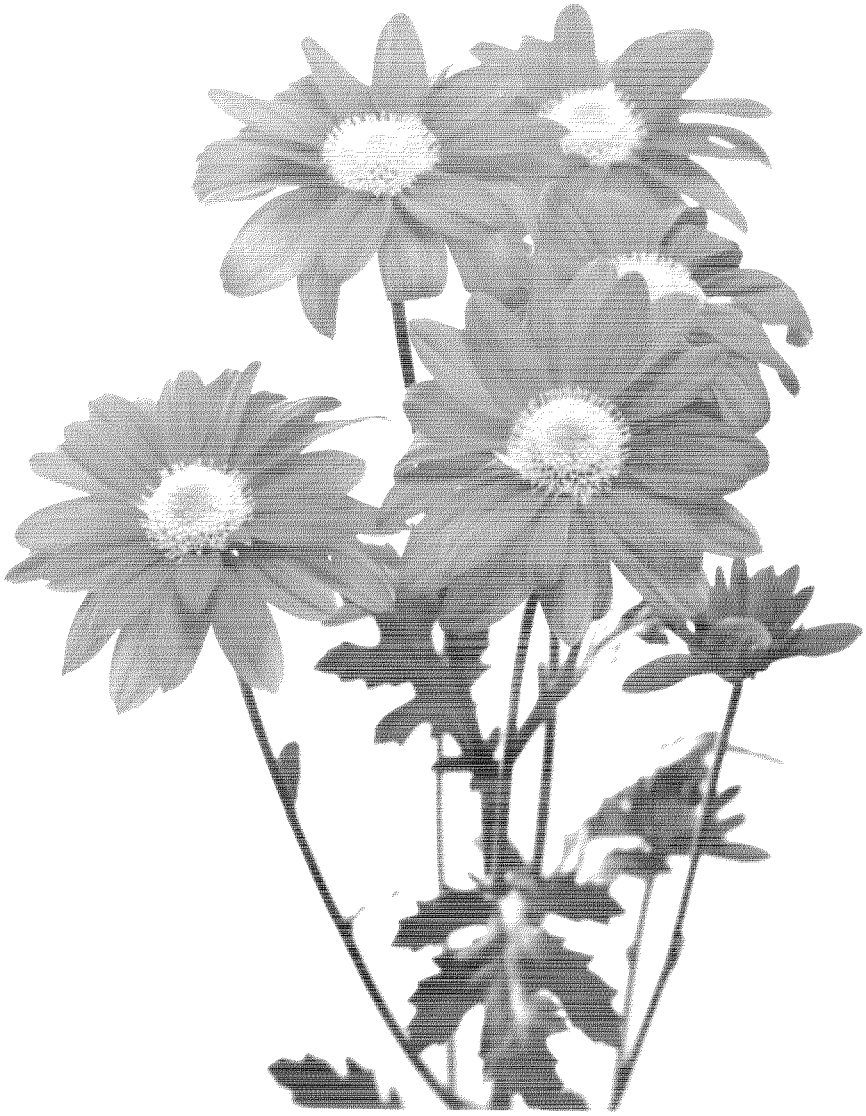

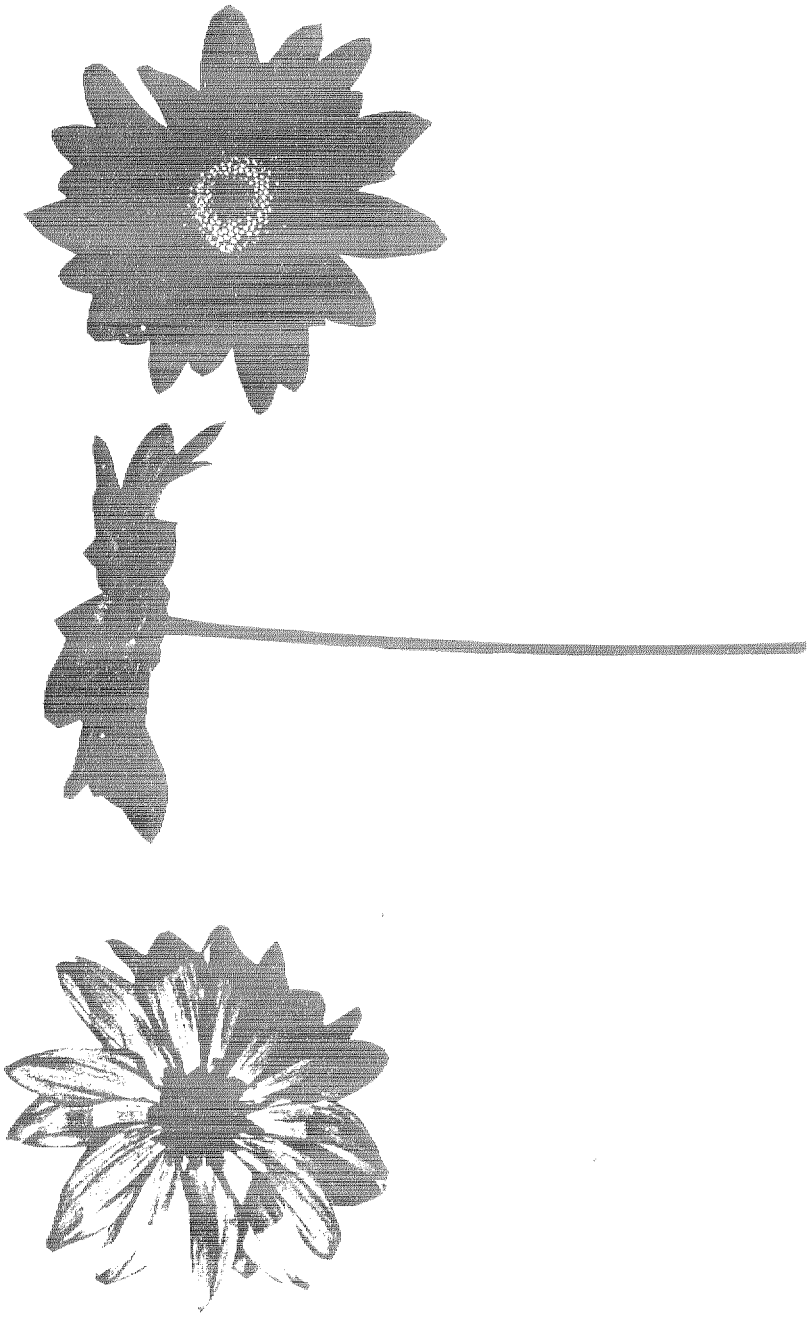

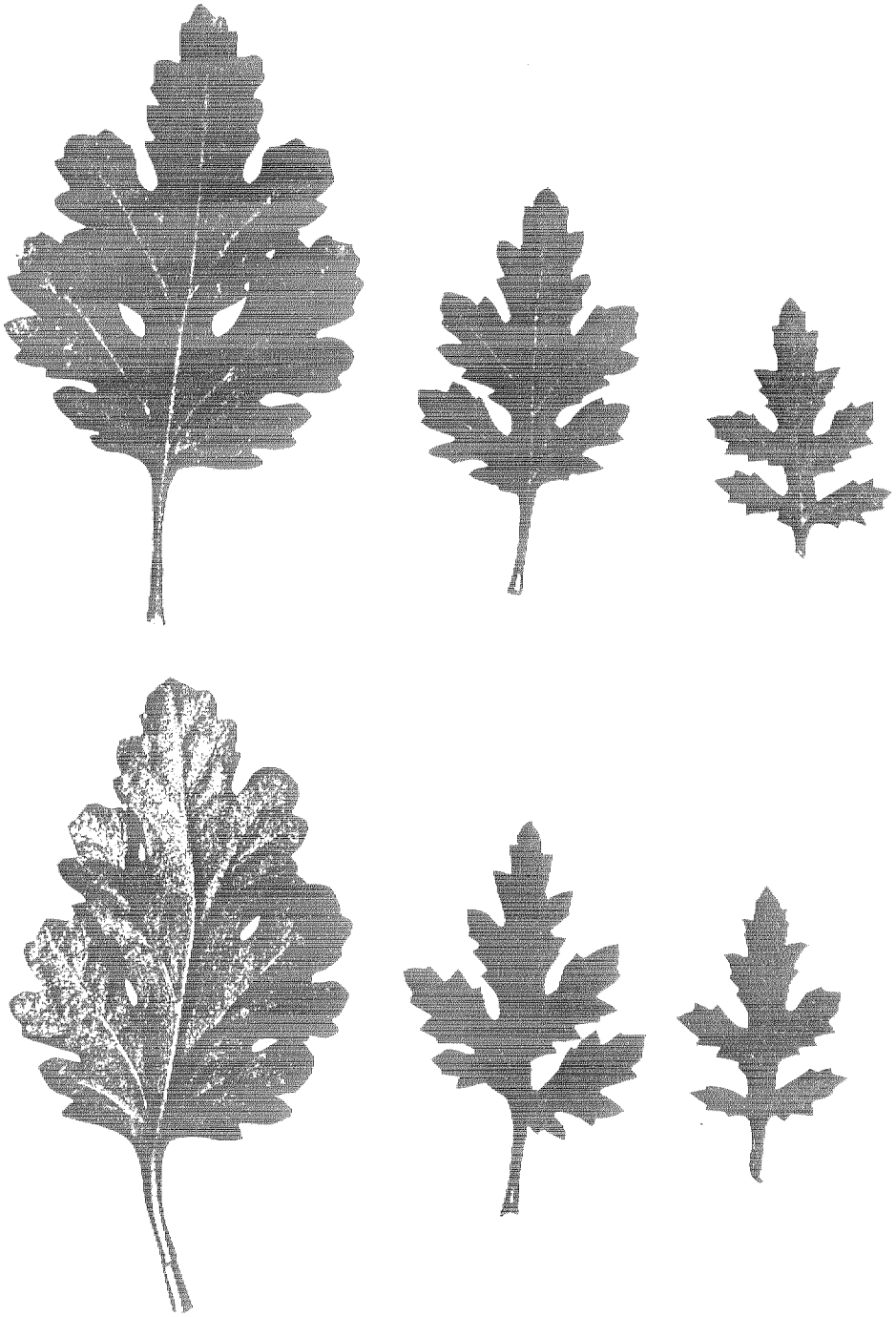

Duffett

[11] Plant 5,202

[45] Mar. 6, 1984

[54] CHRYSANTHEMUM PLANT(FLASH)

[75] Inventor: William E. Duffett, Salinas, Calif.

[73] Assignee: Yoder Brothers, Inc., Barberton, Ohio

[21] Appl. No.: 343,923

[22] Filed: Jan. 29, 1982

[51] Int. Cl.[3] ..... A01H 5/00
[52] U.S. Cl. ..... Plt./74
[58] Field of Search ..... Plt./74

*Primary Examiner*—Robert E. Bagwill
*Attorney, Agent, or Firm*—Schwartz, Jeffery, Schwaab, Mack, Blumenthal & Koch

[57] ABSTRACT

A chrysanthemum plant known by the cultivar name Flash and characterized as to uniqueness by the combined characteristics of flat capitulum form; daisy capitulum type; bronze ray floret color, with minimum color oxidation; diameter across face of capitulum ranging from 70 to 80 mm. at maturity; uniform eight week photoperiodic flowering response to short days; long peduncle length; medium plant height when grown single stem, 10 to 20 cm. peduncles on open, normally terminal sprays with slow development of tight green discs, and 13° C. minimum temperature tolerance for initiation and development of flowering buds.

3 Drawing Figures

The present invention comprises a new and distinct cultivar of *Chrysanthemum morifolium*, Ramat., hereinafter referred to by the cultivar name Flash.

Flash is a product of a planned breeding program which had the objective of creating new chrysanthemum cultivars for cut spray, low temperature tolerant mum programs with daisy capitulum type, bronze ray floret color, eight week flowering response, and with the ability to produce commercially acceptable quality in year round programs. Such traits in combination were not present in previously available commercial cultivars.

Flash was originated from a hybridization made in a controlled breeding program in Salinas, Calif. in 1977. The female parent was #74108007, an unnamed bronze daisy, originated from a cross between two unnamed seedlings. The male parent of Flash was #74077002, an unnamed pink daisy, originated from a cross between two unnamed seedlings. Both parents are unpatented.

Flash was discovered and selected as one flowering plant within the progeny of the stated parentage by William E. Duffett on Aug. 25, 1977 in a controlled environment in Salinas, Calif.

The first act of asexual reproduction of Flash was accomplished when vegetative cuttings were taken from the initial selection in February, 1978 in a controlled environment in Salinas, Calif. by a technician working under formulations established and supervised by William E. Duffett.

Horticultural examination of selected units initiated Feb. 21, 1979 has demonstrated that the combination of characteristics as herein disclosed for Flash are firmly fixed and are retained through successive generations of asexual reproduction.

Flash has not been observed under all possible environmental conditions. The phenotype may vary significantly with variations in environment such as temperature, light intensity, and day length. The following observations, measurements and comparisons describe plants grown in Salinas, Calif. under greenhouse conditions which approximate those generally used in commercial practice.

The following traits have been repeatedly observed and are determined to be basic characteristics of Flash which in combination distinguish this chrysanthemum as a new and distinct cultivar:

(1) flat capitulum form;

(2) daisy capitulum type;

(3) bronze ray floret color with minimum color oxidation;

(4) diameter across face of capitulum ranging from 70 to 80 mm. at maturity;

(5) uniform eight week photoperiodic flowering response to short days;

(6) long peduncle length, ranging from 10 to 20 cm.;

(7) medium plant height, 60 to 90 cm., when grown from a rooted cutting with no long days for March through November flowerings;

(8) 13° C. minimum temperature tolerance for initiation and development of flowering buds; and (9) slow development of tight yellow-green discs devoid of pollen.

Of the many commercial cultivars known to the present inventor, the most similar in comparison to Flash is Amber (disclosed in U.S. Plant Pat. No. 3,969). Reference is made to attached Chart A which compares certain characteristics of Flash to those same characteristics of Amber.

In comparison to Amber, Flash has more intense, longer lasting color, shorter plant height and more rapid flowering response. The capitulum size and form, capitulum type and peduncle length of Flash are similar to those same characteristics of Amber.

The accompanying photographic drawings show typical inflorescence and foliage characteristics of Flash, with colors being as nearly true as possible with illustrations of this type. Sheet 1 is a color photograph of Flash. Sheet 2 is a black and white photograph showing three views of the inflorescence of Flash. Sheet 3 is a black and white photograph showing the foliage of Flash at three stages of growth.

In the following description, color references are made to The Royal Horticultural Society Colour Chart. The color values were determined between 11:00 and 11:30 A.M. on Oct. 21, 1981 under 150 foot-candle light intensity at Salinas, Calif.

Classification:

*Botanical.*—*Chrysanthemum morifolium,* Ramat., cv FLASH.

*Commercial.*—Cut daisy spray.

I. Inflorescence:

A. *Capitulum.*—Form: Flat. Type: Single. Diameter across face: 70 to 80 mm.

B. *Corolla of ray florets.*—Color (abaxial): Brief expression of 42A-B, followed by rapid oxidation to 171-A over 167-A. Color (adaxial): 172-C streaked heavily with 167-A.

C. *Corolla of disc florets.*—Color (immature): Approximately 144-A. Color (mature): 12-A.

D. *Reprodutive organs.*—Androecium: Present discs florets only, scant pollen. Gynoecium: Present both ray and disc florets.

II. Plant:

A. *General appearance.*—Height: Medium; 60 to 90 cm. as a flowering plant from a rooted cutting with no long days for March through November flowerings, and maintaining a minimum nightly 14 hour continuous dark period.

B. *Foliage.*—Color (abaxial): Approximately 137-A. Color (adaxial): Approximately 138-A. Shape: Deeply lobed and coarsely serrated.

CHART A

COMPARISON OF FLASH AND AMBER

| CULTIVAR | RAY FLORET COLOR | CAPITULUM FORM AND TYPE | PLANT HEIGHT |
|---|---|---|---|
| FLASH | Bronze with minimum color oxidation | Flat Daisy | Medium 60 to 90 cm. |
| AMBER | Bronze with minimum color oxidation | Flat Daisy | Tall 70 to 95 cm. |

CHART A-continued

COMPARISON OF FLASH AND AMBER

| CULTIVAR | DIAMETER ACROSS FACE OF CAPITULUM | FLOWERING RESPONSE PERIOD | PEDUNCLE LENGTH |
|---|---|---|---|
| FLASH | 70 to 80 mm. | 8 Week | Long 10 to 20 cm. |
| AMBER | 65 to 80 mm. | 9 Week | Long, 13 to 17 cm. |

COMPARISONS MADE OF PLANTS GROWN AS SINGLE STEM CUT SPRAYS IN SALINAS, CALIFORNIA

I claim:

1. A new and distinct plant of *Chrysanthemum morifolium,* Ramat., known by the cultivar name Flash, as described and illustrated, and particularly characterized as to uniqueness by the combined characteristics of flat capitulum form; daisy capitulum type; bronze ray floret color, with minimum color oxidation; diameter across face of capitulum ranging from 70 to 80 mm. at maturity; uniform eight week photoperiodic flowering response to short days; long peduncle length; medium plant height when grown single stem; 10 to 20 cm. peduncles on open, normally terminal sprays; slow development of tight green discs, and 13° C. minimum temperature tolerance for initiation and development of flowering buds.

* * * * *